US012758121B2

(12) United States Patent
Brightling et al.

(10) Patent No.: US 12,758,121 B2
(45) Date of Patent: Oct. 13, 2026

(54) BREATH SAMPLER

(71) Applicant: Loughborough University, Loughborough (GB)

(72) Inventors: Christopher Brightling, Leicester (GB); Paul Thomas, Loughborough (GB); Dahlia Salman, Loughborough (GB)

(73) Assignee: LOUGHBOROUGH UNIVERSITY, Loughborough (GB)

( * ) Notice: Subject to any disclaimer, the term of this patent is extended or adjusted under 35 U.S.C. 154(b) by 650 days.

(21) Appl. No.: 18/002,018

(22) PCT Filed: Jun. 14, 2021

(86) PCT No.: PCT/GB2021/051474
§ 371 (c)(1),
(2) Date: Dec. 15, 2022

(87) PCT Pub. No.: WO2021/255419
PCT Pub. Date: Dec. 23, 2021

(65) Prior Publication Data
US 2023/0301547 A1 Sep. 28, 2023

(30) Foreign Application Priority Data
Jun. 16, 2020 (GB) ..................................... 2009153

(51) Int. Cl.
*A61B 5/097* (2006.01)

(52) U.S. Cl.
CPC .................................... *A61B 5/097* (2013.01)

(58) Field of Classification Search
None
See application file for complete search history.

(56) References Cited

U.S. PATENT DOCUMENTS 6,578,571 B1 * 6/2003 Watt .................. A61M 15/0016 128/200.14
8,596,273 B2 * 12/2013 Burz ................. A61M 16/0622 128/206.28
(Continued)

FOREIGN PATENT DOCUMENTS

DE 4127599 A1 2/1993
EP 0127259 A1 12/1984
(Continued)

OTHER PUBLICATIONS

Intention to Grant cited in related European Application Serial No. 21735378.8 dated Jun. 19, 2024.
(Continued)

*Primary Examiner* — Michael R Bloch
(74) *Attorney, Agent, or Firm* — Brian J. Colandreo; Jeffrey T. Placker; Holland & Knight LLP

(57) ABSTRACT

A device (100) is disclosed for obtaining a breath sample from a patient, The device comprises a mask or mouthpiece (101) for receiving breath from a patient; an outlet (102) through which breath is exhausted from the device (100); a sampler (110); and a sample container (113). The sampler (110) comprises a distal portion configured to protrude into a flow of breath from the mask or mouthpiece (101), and a sampler opening (118) in the distal portion for obtaining a breath sample. The sample container (113) is in communication with the sampler (110) for receiving the breath sample from the sampler (110).

18 Claims, 11 Drawing Sheets

(56) References Cited

U.S. PATENT DOCUMENTS

| | | | | |
|---|---|---|---|---|
| 8,821,621 | B2 * | 9/2014 | Dwyer | G01N 21/783 55/DIG. 35 |
| 2003/0109794 | A1 * | 6/2003 | Phillips | G01N 1/2214 977/905 |
| 2004/0210154 | A1 | 10/2004 | Kline | |
| 2006/0249160 | A1 * | 11/2006 | Scarberry | A61B 5/6803 128/206.28 |
| 2008/0029098 | A1 * | 2/2008 | Ottestad | A62B 7/12 128/205.12 |
| 2012/0285461 | A1 | 11/2012 | Pierro et al. | |
| 2012/0289851 | A1 * | 11/2012 | Varga | A61B 5/097 600/532 |
| 2014/0128760 | A1 | 5/2014 | Saunders | |
| 2014/0276100 | A1 | 9/2014 | Satterfield et al. | |
| 2014/0358019 | A1 | 12/2014 | Johnson | |
| 2017/0035326 | A1 | 2/2017 | King-Smith | |
| 2018/0043121 | A1 | 2/2018 | Goulitski | |
| 2018/0146886 | A1 | 5/2018 | Leard et al. | |

FOREIGN PATENT DOCUMENTS

| | | | |
|---|---|---|---|
| EP | 3202321 | A1 | 8/2017 |
| JP | 02-098337 | A | 4/1990 |
| JP | 2005-512067 | A | 4/2005 |
| WO | 0201182 | A1 | 1/2002 |
| WO | 2015200926 | A1 | 12/2015 |

OTHER PUBLICATIONS

International Search Report and Written Opinion of related application Serial No. PCT/GB2021/051474 issued on Sep. 9, 2021.

UK Intellectual Property Office Search Report issued in Application No. GB2009153.4 on Dec. 11, 2020.

Office Action cited in related European Application Serial No. 21735378.8 dated Jan. 2, 2024.

Japanese Office Action issued in the related Application Serial No. 2022-577398 dated Jul. 15, 2025.

Japanese Office Action issued in the related Application Serial No. 2022-577398 dated Mar. 25, 2025.

* cited by examiner

BREATH SAMPLER

CROSS-REFERENCE TO RELATED APPLICATIONS

This application is a U.S. National Stage of International Patent Application No. PCT/GB2021/051474, filed 14 Jun. 2021, which claims priority to Great Britain Patent Application No: 2009153.4, filed on 16 Jun. 2020, the disclosures of which are incorporated herein by reference in their entirety.

FIELD OF THE INVENTION

The present invention relates to a breath sampler for facilitating analysis of breath samples, and a method for sampling breath.

BACKGROUND

Breath sampling is a promising technique for facilitating non-invasive diagnosis and health monitoring. Volatile organic compounds (VOCs) are present in breath, which result from both metabolic processes in the cells of the body and from the microbiome inhabiting the body. These metabolic processes may be affected/disrupted by disease conditions, resulting in changes in the VOC profile present in breath. It is therefore possible to identify disease conditions by analysis of VOC profiles in sampled breath. Changes in VOC profile may provide biomarkers that enable specific disease conditions to be identified. This is a promising and active area of research.

Obstacles to widespread adoption of breath sampling as a diagnostic technique include sampling methodology. Different methodologies for breath sampling lead to significant variation in data obtained from subsequent analysis of the samples. Increasing availability of a high quality breath sampling methodology would stimulate development of breath sampling as a diagnostic technique.

An example of an existing breath sampling device is disclosed in US2017/303822.

It is challenging to obtain a breath sample that facilitates reliable analysis of VOC compounds in breath. The VOC mass present in a typical breath sample is low, and precise analysis of the VOC profile can easily be confounded by contaminants in the breath sample. It is also desirable that a breath sampler is easy to use and maintain, and affordable enough to deploy at scale.

Although considerable progress in breath sampling has been made, there is room for improvement in a number of areas.

SUMMARY

According to a first aspect, there is provided a device for obtaining a breath sample from a patient, comprising:

- a mask or mouthpiece for receiving breath from a patient;
- an outlet through which breath is exhausted from the device;
- a sampler, comprising:
  - a distal portion configured to protrude into a flow of breath from the mask or mouthpiece,
  - a sampler opening in the distal portion for obtaining a breath sample; and
- a sample container in communication with the sampler for receiving the breath sample from the sampler.

Drawing the sample into the sample container (e.g. a thermal desorption tube, needle trap, arrow sampler or solid phase microextraction fibre) through a sampler may confer advantages in certain embodiments. In some embodiments, the sampler may be configured to approximate isokinetic sampling, thereby reducing contamination of the analytical signature of the breath sample (for example due to collection of water and aerosols). In some embodiments, the sampler may reduce contact with the sample container during assembly and disassembly of the sample container in the breath sampling device.

The sampler opening may be disposed in a sidewall of the distal portion. In certain embodiments this may better approximate isokinetic sampling conditions.

The sampler opening may be spaced apart from a tip of the distal portion. A tip of the distal portion may comprise an end flange. In certain embodiments this may help prevent contact with the sampler opening and/or improve approximation of isokinetic sampling conditions.

The distal portion of the sampler may be substantially tube shaped (e.g. cylindrical).

The sampler may comprise a proximal portion configured to engage with the sample container.

The proximal portion of the sampler may be configured to seal against the outside of the sample container.

The sampler may comprise an internal groove and an O-ring seal disposed in the internal groove for forming a seal with the outside of the sample container.

The sample container may be removeable from the breath sampling device by pulling on the sampler. In certain embodiments this enables the sample container to be handled during installation and removal in the breath sampling device via the sampler, thereby avoiding contact with the sample container.

The device may comprise a filter, downstream of the sampler (such as a HEPA filter). This may avoid or reduce the potential for particles (e.g. virus particles) in the patient's breath from exiting the breath sampling device.

The device may further comprise a handle for holding the device. The sample container and sampler may be housed by the handle The sampler is configured for sealing engagement with the handle.

The sampler may comprise an external groove and an O-ring seal disposed in the external groove for forming a seal with the handle.

The handle may comprise a hand operable clip for locking and unlocking engagement of the handle with the mask or mouthpiece The handle may comprise an inner sleeve and an outer sleeve, and the handle may be securable to the mask or mouthpiece by clamping the mask or mouthpiece between the inner and outer sleeve.

The filter may be received by the inner sleeve (e.g. by a push fit).

The handle may comprise a pressure probe for communicating a fluid pressure to a pressure sensor.

The handle may comprise an intake air conduit, for providing to the mask or mouthpiece for the patient to breath.

According to a second aspect, there is provided an air purifier for a breath sampling device, the air purifier comprising at least one cartridge filter (which may be cylindrical) configured to purify air provided to the breath sampling device.

The cartridge filters may be standard cartridge filters (e.g. NATO 40 mm standard gas filters such as an AX filter cartridge). In certain embodiments, the use of (commercially available) cartridge filters may reduce the cost associated with using and servicing the air purifier.

According to a third aspect, there is provided a breath sampling system, comprising the device according to the first aspect, and the air purifying system according to the second aspect.

The air purifier may comprise two cartridge filters, configured for parallel flow.

The air purifier may comprise three (or more) cartridge filters, which may be configured for parallel flow. More cartridge filters in parallel may provide for enhanced flow rate and improved air purification by removal of volatile organic compounds.

The air purifier may comprise a hand operated latch for obtaining access to the cartridge filters for replacement of the cartridge filters.

According to a fourth aspect, there is provided a system for transportation of breath sampling consumables, comprising:

- a sample container for receiving a breath sample;
- a first and second end cap for sealing first and second ends of the sample container;
- a case for receiving the capped sample container, the case comprising a first cap socket and a second cap socket; wherein:
- the first cap socket is a pivotable cap socket configured to: pivot between an upstanding and a prone position, and receive the first end cap,
- the second cap socket is configured to receive the second end cap, and
- the pivotable first cap socket and the second cap socket are together arranged to retain the first and second end caps in sealing engagement with the respective first and second ends of the sample container when the first and second end caps are received in the respective first and second cap sockets.

In certain embodiments, this may avoid time consuming sealing procedures for sample containers which are commonly employed in prior art breath sampling methodologies (e.g. involving the use of tools etc).

The first cap socket and second cap socket may be configured to allow a thermal desorption tube, capped by a first and second end cap, to be rotated from a first upstanding position in which the first end cap is received in the first cap socket, to a second prone position in which the second end cap is clipped into the second cap socket.

According to a fifth aspect, there is provided a system for breath sampling, comprising a breath sampling device according to the first aspect, an air purifier according to the second aspect, and a controller configured to control flow of a breath sample through the sample container.

The controller may comprise a sampling port for connection to the sample container and a pressure port for connection to the pressure probe. The controller may comprise a sampling pump for drawing air through the sampling port, and therefore through the sample container. The controller may comprise a pressure sensor for detecting pressure in the breath sampling device via the pressure port. The controller may comprise control logic for controlling the operation of the breath sampling device. The control logic may be configured to control the sampling pump, responsive to the pressure sensor.

According to a sixth aspect, there is provided a method of sampling breath of a patient for analysis, comprising:

- receiving breath from the patient into a breath sampling device via a mask or mouthpiece;
- drawing a sample from a flow of breath through the breath sampling device into a sample container via a sampler that is engaged with an end portion of the sample container.

The breath sampling device may be in accordance with the first aspect. The method according to the sixth aspect may comprise using any of the breath sampler, air purifier and breath sampling system features described herein.

The method may comprise providing a purified supply of air to the breath sampling device for the patient to breathe. The supply of purified air may be used to maintain a positive pressure in the mask or mouthpiece.

According to a seventh aspect, there is provided a breath sampling system comprising:

- a device for obtaining a breath sample from a patient, comprising:
  - a mask or mouthpiece for receiving breath from a patient;
  - a sample container for receiving a sample of breath from the patient;
- a controller comprising a sample port and a sample pump configured to draw air through the sample port;
- a mode selection valve in fluid communication with the sample pump;
- a sample conduit connecting the mode selection valve to the sample container;
- a port for connection to a further sample container, for sampling ambient air;
- wherein the mode selection valve is operable to selectively connect the sample pump with the sample conduit to sample breath into the sample container or to connect the sample pump with the port to sample ambient air into the further sample container.

The device for obtaining a breath sample may further comprise an outlet through which breath is exhausted from the device. The outlet may be situated on the mask or mouthpiece.

The device for obtaining a breath sample may be in accordance with the first aspect.

The breath sampling system may further comprise an air purifier configured to provide air to the mask or mouthpiece. The air purifier may comprise at least one cartridge filter (which may be cylindrical) configured to purify air provided to the mask or mouthpiece.

The air purifier may be in accordance with the second aspect.

The mask or mouthpiece may be fluidly coupled to the air purifier by a flexible tube.

The air purifier and controller may be housed in a container or housing.

The mode selection valve may be housed in a container or housing.

The air purifier, controller and mode selection valve may be housed in the same container or housing. Other components of the breath sampling system may also be housed in the same container or housing. The container or housing may allow for easier transportation of the breath sampling system.

The housing or container may be a briefcase. In some embodiments components of the breath sampling system may be operable without being removed from the housing or container. For example, the controller, air purifier and mode selection valve may be controlled while housed in the container or housing. This may allow for faster set up or easier operation of the system.

The container or housing further may comprise a holding fixture configured to hold the device for obtaining a breathing sample. In some embodiments the container or housing may be a briefcase, and the holding fixture may be a holder on the internal surface of the lid of the briefcase. The holding fixture may make operation of the system more convenient for the user by providing a stowage point for the mask or mouthpiece while the user performs other tasks. This may also prevent the mask or mouthpiece being placed on an unsanitized surface.

The controller may be configured to connect wirelessly with a remote computer.

The remote computer may be a mobile computing device. The mobile computing device may be, for example, a smartphone.

The mobile device may comprise software for controlling the controller and/or the air purifier. The software may be an app that is installed on a smartphone.

The app may be an app configured to run on an iOS™ and/or Android™ smartphone. In some embodiments, the app may allow the user to control the controller and/or air purifier. A user input on the app may be used to control the controller and/or air purifier as required to obtain an environmental sample, a control sample or a breath sample from a patient.

In some embodiments the app may be configured to generate and/or record additional information in relation to samples obtained using the breath sampling system. For example, the user may instruct the controller to obtain an environmental sample, a control sample or a breath sample from a patient using a user input on the app. The app may then record a log regarding the sample. The log may include for example: time and date information of the sample (which may be provided by the smartphone operating system); additional information about the sample regarding the user inputs entered on the app before the sample was obtained (for example sample type); additional information entered manually on the app by the user (for example notes regarding user observations).

The app may generate a reference code that may be used to associate logs on the app with samples taken using the breath sampling system. The reference code may be an alphanumeric sequence that the user writes on the sample after the sample is obtained and correspondingly logged in the app. In some embodiments each sample may have an identification marker (such as a QR code, barcode or alphanumerical sequence) that may be scanned using the app and a camera on the smartphone to find any logs corresponding to each sample.

In some embodiments the app may provide the user with instructions or information regarding the operation of the breath sampling system. For example, the app may provide the user with sequential instructions that guide the user through obtaining an environmental sample, a control sample and then a breath sample with the breath sampling system. Such instructions and information may be provided by the app in a number of languages, selectable by the user.

According to an eighth aspect, there is provided a method for sampling breath of a patient with a breath sampling system, comprising:

- obtaining an environmental sample of ambient air;
- obtaining a control sample with a device for obtaining a breath sample from a patient; and
- obtaining a breath sample from the patient with the device for obtaining a breath sample from a patient.

The breath sampling system may be in accordance with the seventh aspect.

The environmental sample may be taken using a port to sample ambient air and the control sample and breath sample may be taken using a sample conduit connected to a mask or mouthpiece of the device for obtaining a breath sample from a patient, The method may comprise:

- after obtaining the environmental sample and before obtaining the control sample, moving a selection valve from a first position wherein a sample pump is fluidly coupled to the port to sample ambient air to a second position wherein the sampler pump is connected to the sample conduit connected to the mask or mouthpiece.

The method may comprise providing a purified supply of air to the mask or mouthpiece for the patient to breathe. The purified air supply may be provided by an air supply connected to an air purifier. The air supply may be turned on and off as required. The supply may be used to maintain a positive pressure in the mask or mouthpiece.

The method may comprise obtaining the control sample while the device for obtaining a breath sample is stowed in a holding fixture of a container or housing of the breath sampling system.

The method may comprise:

- after obtaining the control sample and before obtaining the breath sample from the patient, removing the device for obtaining a breath sample from the holding fixture and fitting the device onto a patient.

The method may comprise using a mobile computing device to at least partially instruct the breath sampling system to obtain at least one of the samples in response to a user input.

The mobile computing device is a smartphone and the user input involves pressing a button in an app, wherein pressing the button instructs the breath sampling system to obtain one of the samples.

The app may be in accordance with the seventh aspect.

DETAILED DESCRIPTION

Embodiments of the invention will described, purely by way of example, with reference to the accompanying drawings, in which.

Figure 1:
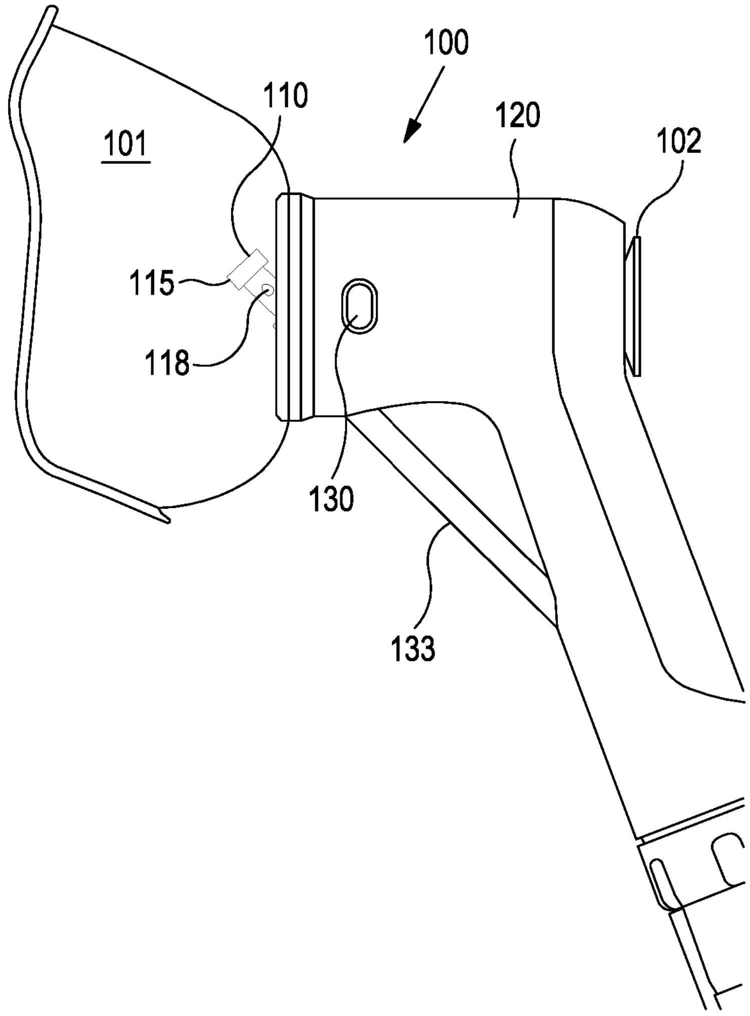
FIG. 1 is a side view of an embodiment of a device for obtaining a breath sample.
Figure 2:
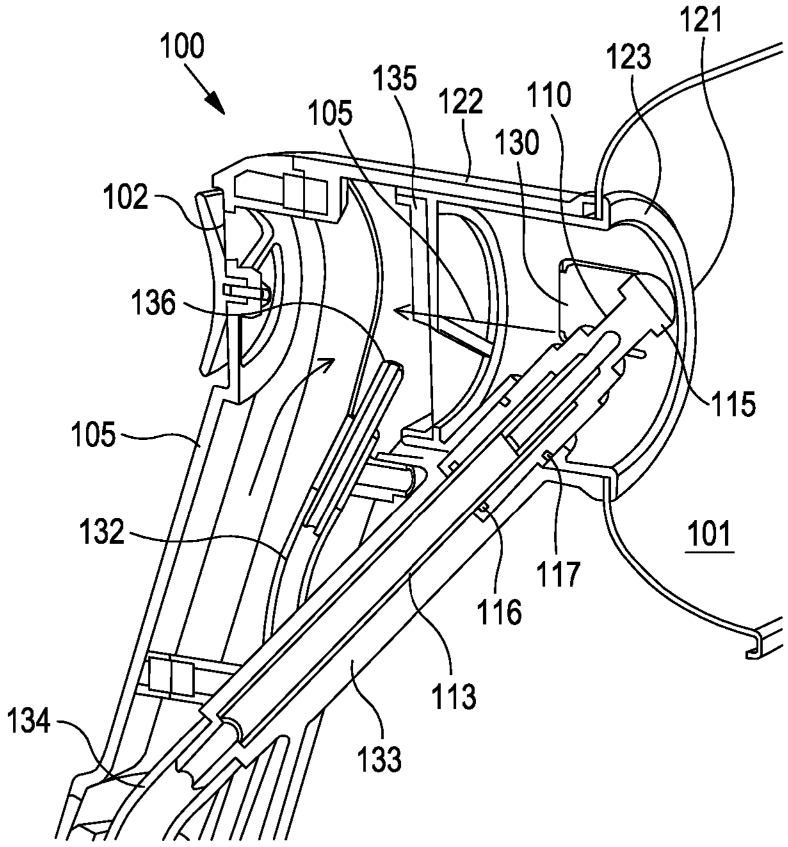
FIG. 2 is a side sectional view of the embodiment of FIG. 1.
Figure 3:
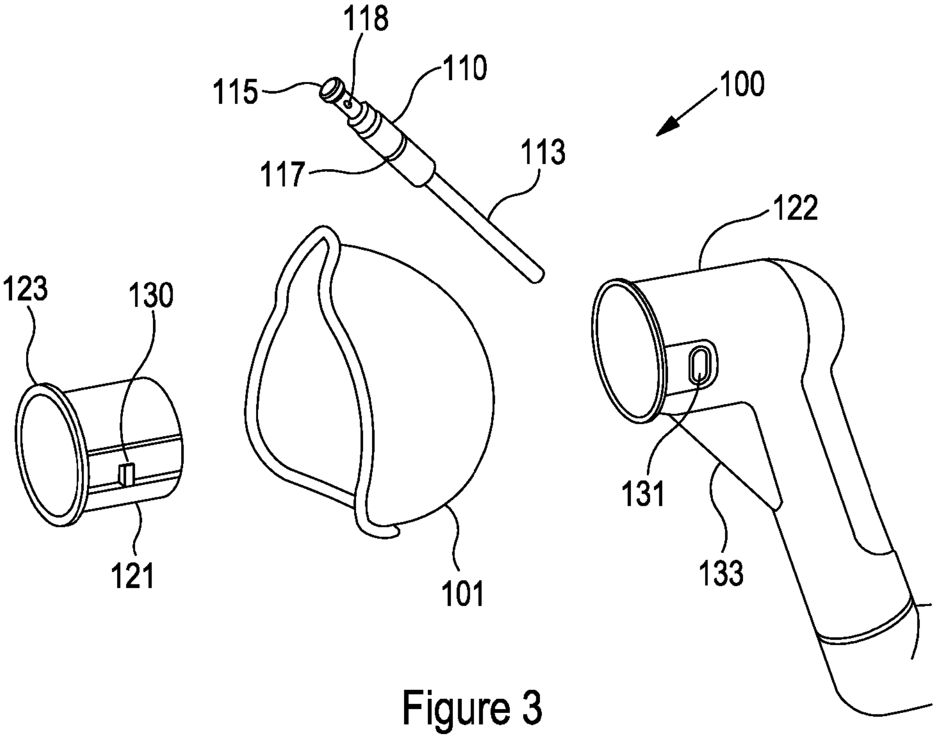
FIG. 3 is an exploded diagram of the example device of FIGS. 1 and 2.

Referring to FIGS. 1 to 5, an example device 100 for obtaining a breath sample from a patient is shown, comprising a mask 101, a handle 120, a sampler 110 and a sample container 113 for receiving a breath sample.

The mask 101 may comprise a flexible material, and is configured to conform to the contours of the patient's face. The mask 101 may be disposable consumable item, replaced for each new patient to be sampled. The mask 101 is detachable from the handle 120, by using a hand operated clip 130 (without the use of tools), which will be described in more detail below.

In use, the patient places the mask 101 over their face, and breathes into the device 100. The breath is received by the mask 101 and channeled into the handle 120. The breath is exhausted from the handle via the outlet 102, which comprises a one-way valve. Air is received into the handle 120 via an intake conduit 105 for the patient to breath in through the mask 101. Optionally, the interior of the mask 101 and handle 120 may be maintained at positive pressure by a pumped flow of air received by the intake conduit 105. The inflowing air may be purified (e.g. to reduce background contaminants in the breath that do not arise from the patient).

The handle 120 houses the sample container 113, which receives a breath sample from the flow of breath into the mask 101. The sample container 113 in this example is preferably a thermal desorption tube 113, but in other embodiments different types of sample container (suitable for sampling VOCs) may be used, including a needle trap, arrow sampler or solid phase microextraction fibre. The sample container 113 may be configured to retain VOCs compounds in breath by reversible adsorption. Subsequent heating of the sample container 113 will release (by desorption) the VOCs for analysis (e.g. using gas chromatography with mass spectrometry detection or GC-MS).

In order to reliably characterise the trace VOCs that are collected in the sample container 113, for example to perform a diagnosis based on biomarkers, it is important that contamination of the sample is avoided. In prior art devices, such contamination has typically been hard to avoid. The applicant has identified that a source of contamination can arise from handling of the sample container 113. Even gloved hands may load the sample container with contaminants on handling, and these contaminants may, in certain cases, confound or obscure accurate profiling of VOC compounds in the breath sample. Certain embodiments of the present device are therefore arranged to minimise contact with the sample container 113 during installation of the sample container 113 in the device 100 and during removal of the sample container 113 from the device 100 (after breath sampling).

A proximal portion of the sampler 110 is configured to engage with the sample container 113 by receiving a portion of the sample container 113 in a recess in the sampler 110. The sampler 110 is provided with a seal 116 that engages with an internal surface of the sampler 110 and an external surface of the sample container 113. In this embodiment the seal 116 comprises an o-ring 116, retained in an internal groove in the sampler 110.

When the sample container 113 is received in sealing engagement with the sampler 110, the sample container 113 can be picked up by holding the sampler 110. The sample container 113 can consequently be handled by holding the sampler 110 rather than the sample container 113, for example to place the sample container 113 in the device 100 and to remove the sample container from the device 100. Placing the sample container 113 in the device may comprise first assembling the sample container 113 in sealing engagement with the sampler 110, then placing the assembled sample container 113 and sampler 110 in the device 100. The sample container 113 is received in a sample container housing 133. The sample container housing is at an acute angle to the direction of breath flow 105 from the mask 101 to the outlet 102 (which may make isokinetic sampling more straightforward to achieve).

The sampler 110 engages with the handle 120 when installed in the device 100. An external o-ring 117 is retained in an external groove 126 of the sampler 110 for forming a seal between the handle 120 and the sampler 110. In the example embodiment, the sampler 110 seals against an inner sleeve 121 of the handle.

The sampler 110 comprises a sampler opening 118 and an internal channel for communicating a breath sample from the sampler opening 118 to the interior of the engaged sample container 113. A sample conduit 134 is connected to the sample container housing 133 to draw a breath sample into the sample container 113 (for instance by the application of a negative pressure to the sample conduit 134).

A further problem in prior art breath sampling devices arises from the velocity of sample flow in the sampling path not being well matched with the velocity of breath through the sampling device. Under such conditions aerosol and condensate droplets may be entrained with the sample. A more representative sample can be obtained when the sampling conditions better approximate the isokinetic sampling condition, in which there is no divergence or convergence of flow lines around the sample inlet.

Figure 4:
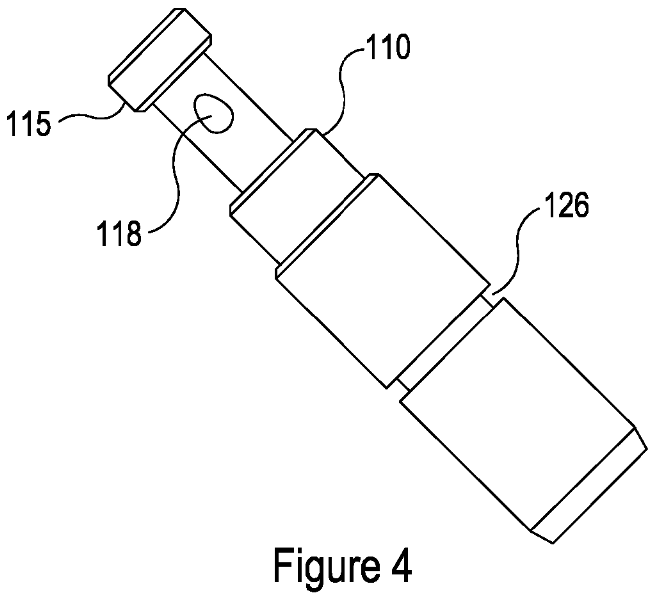
FIG. 4 is a detailed view of a sampler.
Figure 5:
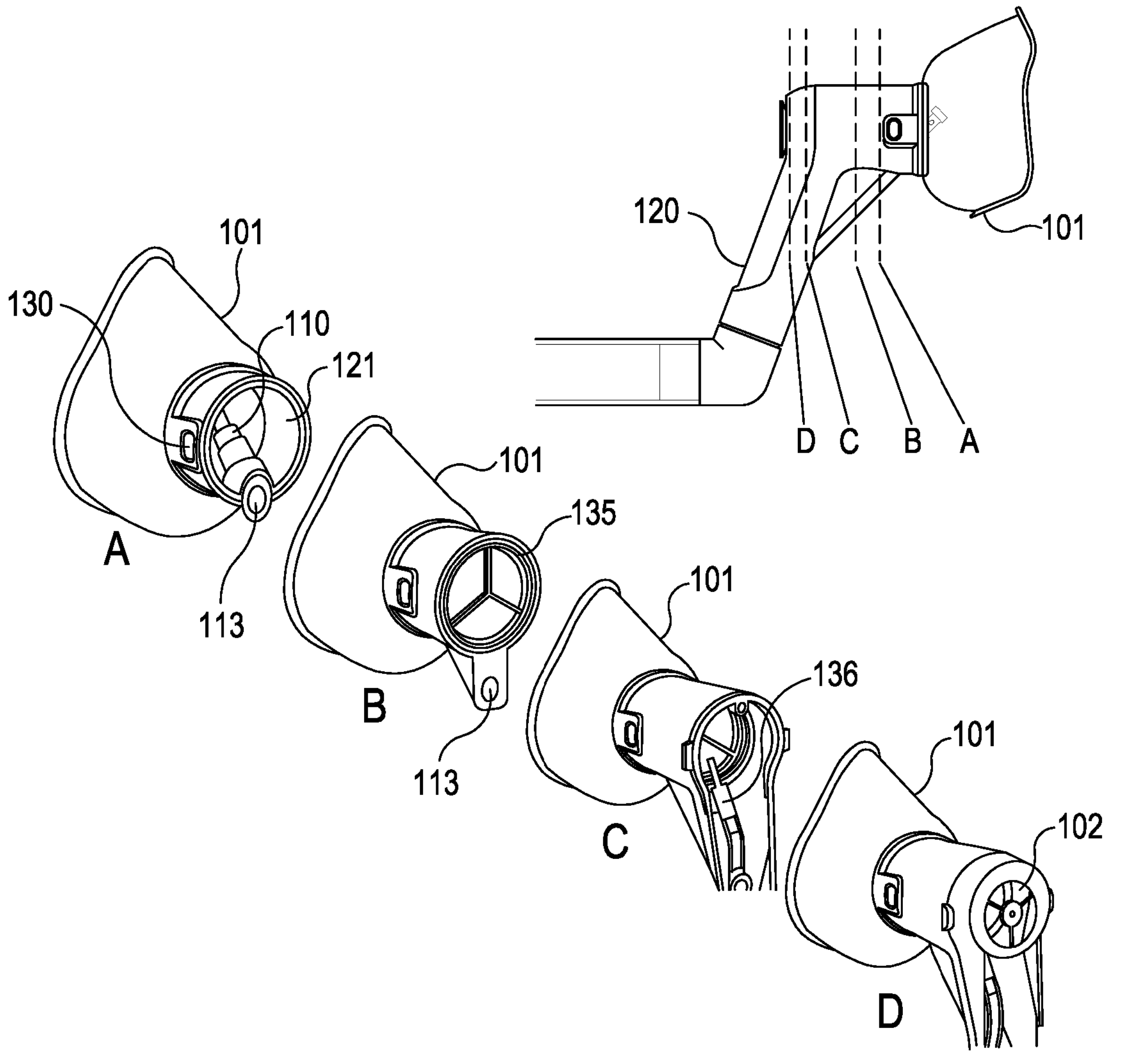
FIG. 5 is sequence of sections showing an end view of the example device.

The applicant has identified that, in certain embodiments, more representative samples may be obtained from a sampler opening 118 that is in a sidewall of the sampler 110, as shown, for example, in FIG. 4. In certain embodiments, the sampler 110 may be provided with a locator (such as a radial protrusion) so that the rotational orientation of the sampler 110 in engagement with the handle 120 is defined, thereby defining the orientation of the sampler opening 118 with respect to the flow of breath through the handle 120. The preferred orientation of the sampler opening 118 may be facing perpendicular to the flow direction of breath through the handle 120, as shown in FIG. 1. The sampler opening 118 may be arranged to be located substantially in a central region of the breath flow path from the mask 101 to the outlet 102.

The sampler opening 118 is spaced apart from a tip of the sampler 110, so that the sampler 110 can easily be handled without contact with the sampler opening 118. This helps reduce contamination of any breath samples through handling. An end flange 115 is provided at the distal tip of the sampler 110, which further helps reduce the potential for contact with the sampler opening 118 by providing purchase for gripping and removing the sampler 110 and sample container 113.

The handle 120 comprises an inner sleeve 121 and an outer sleeve 122. The inner sleeve 121 is cylindrical and concentric with the outer sleeve 122. The inner sleeve 121 comprises a latch 130 which is resiliently biased outwards. The outer sleeve 122 comprises an opening that is configured to receive a portion of the latch. As the inner sleeve 121 is pushed into the outer sleeve, the latch 130 engages with the outer sleeve 122 to lock the inner sleeve 121 in position. The mask 101 is clamped between a flange 123 of the inner sleeve 121 and the outer sleeve 122 when the inner sleeve 121 is locked in position. The inner sleeve 121 can be detached from the outer sleeve 122 by pinching the latch on either side of the handle with one hand, thereby facilitating separation of the inner sleeve 121 from the handle 120, and the mask or mouthpiece from the handle 120. Removal of the sampler 110 and sample container 113 does not require that the inner sleeve 121 is disengaged from the handle 120.

A filter 135 may be provided between the mask 101 and the outlet 102, preferably downstream of the sampler 110. In the example embodiment, a filter 135 is provided that is received in a recess in the inner sleeve 121. The filter 135 may, for example, comprise a HEPA filter. This may easily be replaced (without using tools) by detaching the inner sleeve 121 from the handle, as described above.

In order to facilitate control of sampling of breath at appropriate times in a breathing cycle of the patient (e.g. by controlling a pump connected to the sample conduit 134) a pressure sensing probe 136 is provided, for communicating the pressure in the handle to a pressure sensor (via the pressure conduit 132), which may be in a controller external to the breath sampling device. Separating control systems from the breath sampler may decrease the cost of ownership and use of the sampling system as a whole, since the breath sampling device can readily be broken down and cleaned/sterilised for re-use, and the controller remains free from potential contact with the patient and contamination. The breath sampling device 100 may be free from electronics and sensors.

Figure 6:
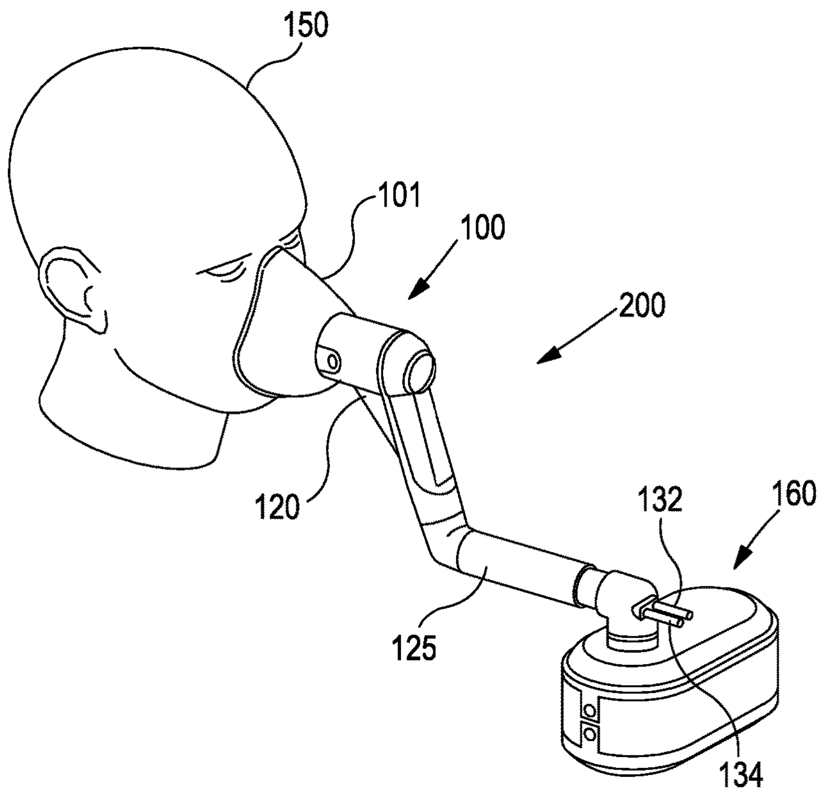
FIG. 6 shows an example system for obtaining a breath sample, comprising the device of FIGS. 1 to 5 and an air purification system.

Referring to FIG. 6, a system 200 is shown, comprising the breath sampling device 100 shown in FIGS. 1 to 5, and further comprising an intake conduit 125 connecting the breath sampling device 100 to an air purifier 160. The breath sampling device 100 is shown worn by a patient 150. The pressure conduit 132 and sample conduit 134 exit the intake conduit 125 before the air purifier 160, for connection to a control system. Such a control system may include a microprocessor, pump and pressure sensor, and may be configured to control sampling of breath.

The air purifier 160 receives air (e.g. from an air pump, 170 in FIG. 12), and removes any background contaminants (including VOCs), which enables improved detection of biomarkers in breath samples (by removing background contaminants).

Figure 7:
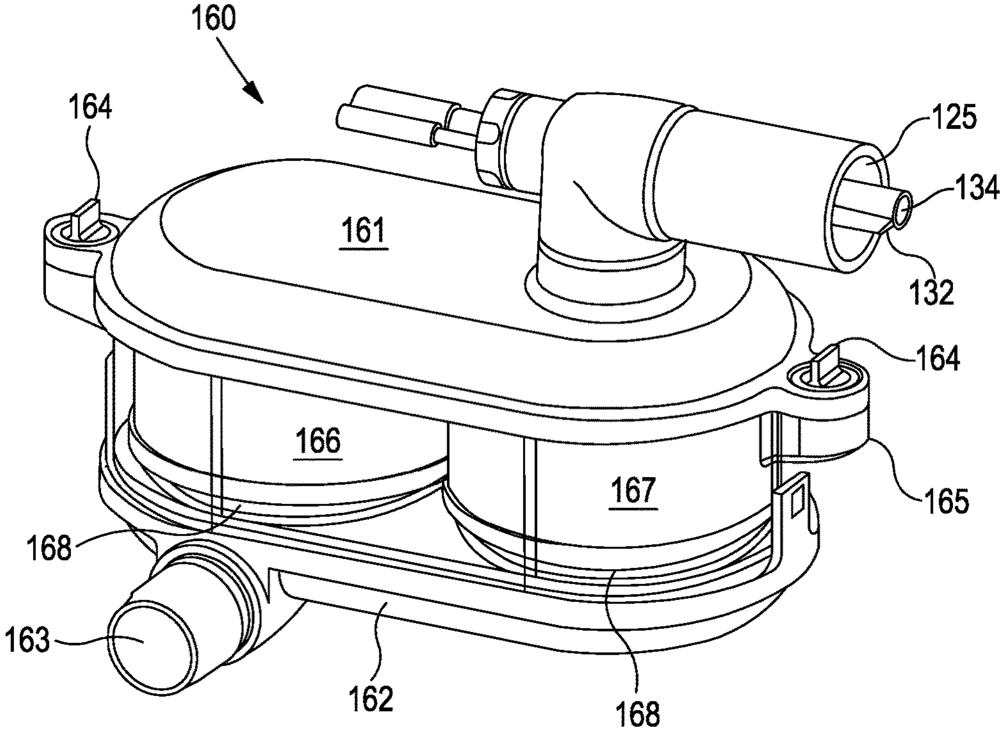
FIG. 7 shows a detailed view of an example air purification system according to an embodiment.

The air purifier 160 is shown in more detail in FIG. 7, and comprises an intake manifold 162, outlet manifold 161, first filter cartridge 166, second filter cartridge 167, and housing 165.

The intake manifold 162 comprises an inlet 163 by which air is provided (e.g. from an air pump) to the air purifier 160. The air is provided from the intake manifold 162 to the first and second filter cartridge 166, 167, which are configured in a parallel configuration. The first and second filter cartridge may comprise standard filter cartridges (e.g. conforming with EN14387A1 and/or meeting the requirements of European Directive 89/686 EEC, such as the Moldex A1 or a compatible cartridge). The first and second filter cartridge 166, 167 may therefore be relatively low cost and straightforward to replace (in contrast with prior art proprietary air purification systems, which are typically very expensive to service).

The outlet manifold 161 receives purified air from the first and second cartridges 166, 167, and provides this to the intake conduit 125, which supplies the breath sampling device 100 with purified air. The pressure conduit 132 and sample conduit 134 exit the intake conduit 125 adjacent to the outlet manifold 161, for connection to a control system.

The intake manifold 162 and the outlet manifold 161 are clipped to the housing 168. The outlet manifold is clipped to the housing 168 with a rotating cam lock system 164, facilitating straightforward removal of the outlet manifold 162 for replacement of the filter cartridges 166, 167.

Figure 8:
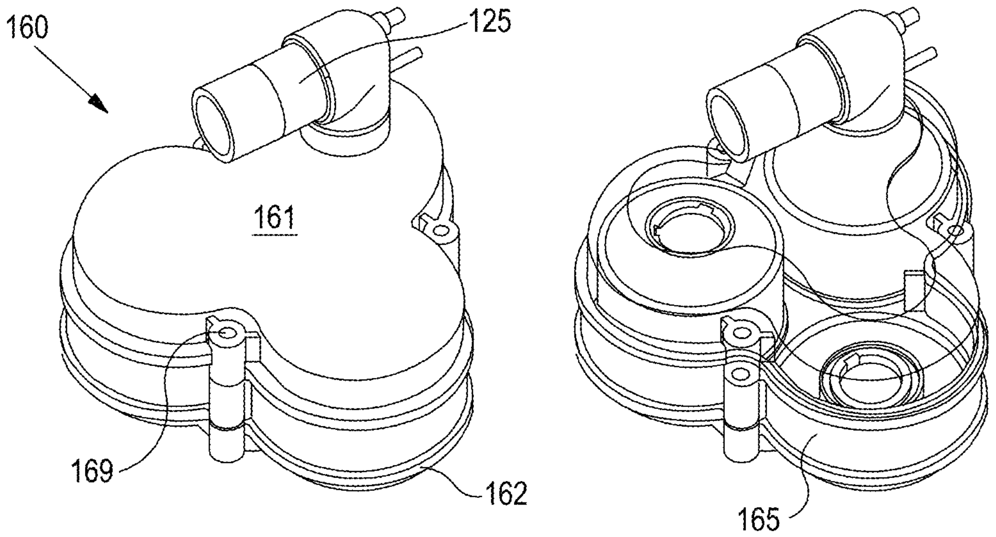
FIG. 8 shows an alternative example air purification comprising three cartridge filters according to an embodiment.

FIG. 8 shows an example air purification system 160 similar to that shown in FIG. 7. The left-hand side of the figure shows the air purification system 160 comprising outlet manifold 161, intake manifold 162, intake conduit 125 and housing 165. The right-hand side of the figure shows the air purification system 160 with the outlet manifold 161 illustrated transparently for clarity. The air purification system is configured to house three cartridge filters connected by the outlet manifold 161 and intake manifold 162 for parallel flow (although only two cartridges are shown in this figure). Three cartridges may provide higher flow rate and improved filtration of volatile organic compounds as compared to systems with two cartridges. In FIG. 8 the outlet manifold 161 is coupled to the housing 165 and the inlet manifold 162 using fasteners such as screws. Co-axial holes 169 are provided in the outlet manifold 161, housing 165 and inlet manifold 162 for receiving such fasteners. Alternatively, an arrangement more like that of FIG. 7 may be used.

Figure 9:
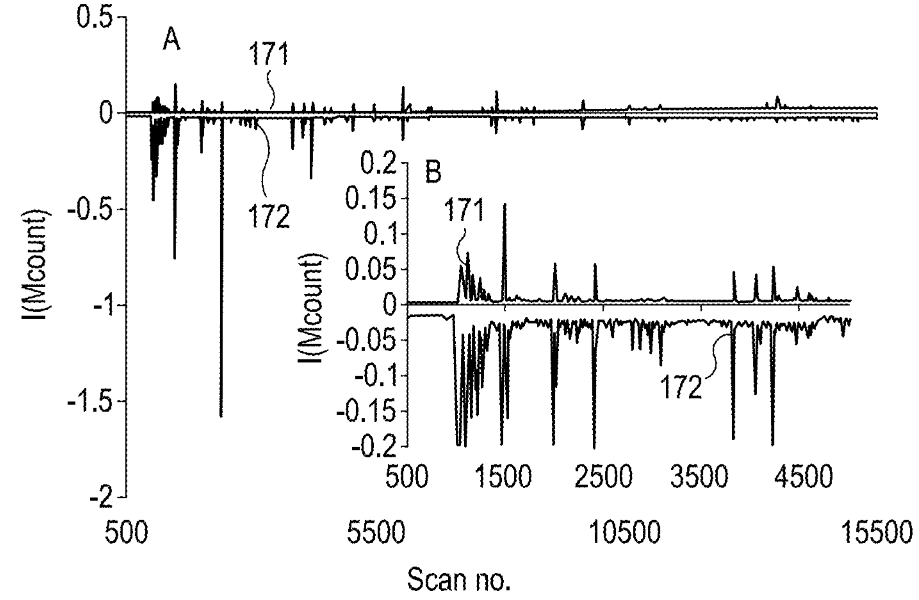
FIG. 9 shows a gas chromatography-mass spectrometry analysis (GC-MS), comparing results obtained from an air purification system according to an embodiment with results obtained from a prior art device.

FIG. 9 illustrates the effectiveness of an air purification system according to an embodiment (similar to that shown in FIG. 7), showing a count per scan (inverted) for a prior art breath sampling air purification system 172 and for an air purifier 160 in accordance with an embodiment 171. The level of contaminants present in the purified air is substantially lower for the air purifier according to an embodiment.

Figure 10:
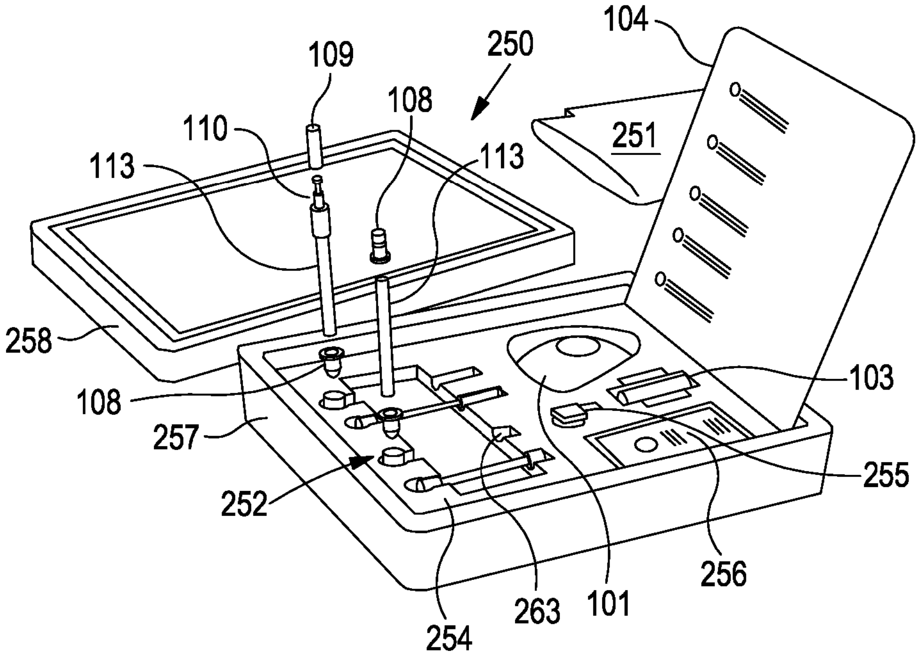
FIG. 10 shows a system for transportation of breath sampling consumables.
Figure 11:
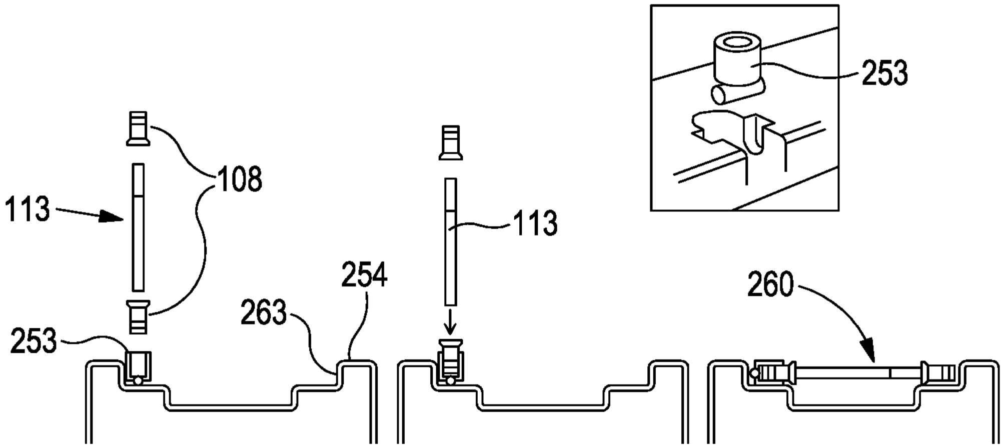
FIG. 11 illustrates a sample container locking in place in a prone position in a sample case.

FIGS. 10 and 11 show a system 250 for transportation of breath sampling consumables, comprising an insulated case (with a base 257 and lid 258), tray 254, pivotable cap sockets 252, 253 fixed cap sockets 263 and coolant vessel 251. The consumables for storage comprise at least one of: sample containers 113, samplers 110, non-transient machine readable instructions 255 (e.g. a user manual for a breath sampling device or system, or instructions for configuring a computer to control a breath sampling system) for example on a USB drive, mask 101, mouthpiece 103, human readable instructions 256, 104.

The system 250 is configured to enable a sample container 113 to be sealed and engaged with the tray 254 with the minimum of contact with the sample container 113. For example, the tray 254 includes slots for sample containers 113 that are engaged with a sampler 110. A sample container cap 108 may be placed in a pivotable socket 252, 253, and the exposed end of the sample container 113 inserted into the end cap (while holding the sampler 110). A sampler cap 109 may subsequently be placed over the sampler 110 to seal the sampler opening 118. The sample container 113 and sampler 110 may then be pivoted (as indicated by arrow 260 in FIG. 10) so that the sampler cap 109 is received and retained in place by a fixed socket defined in the tray 254.

Alternatively, the sampler 110 may be removed from the sample container 113, and sample container caps 108 used to seal each end of the sample container 113. One of the tube caps 108 may again be received in a pivotable socket 252, and then the sample container 113 pivoted to engage the other end cap with a stationary socket 263. This system makes it straightforward to cap the sample containers 113 with the minimum of effort, and with minimal contact and hence reduced risk of contamination of the sample.

In order to ensure that VOCs are retained within the sample containers 113 and remain stable during transit, a coolant bag may be provided in the system to maintain a low temperature in the interior of the insulated case. The coolant bag may, for example, contain a suitable phase change material such as water or sodium polyacrylate.

Figure 12:
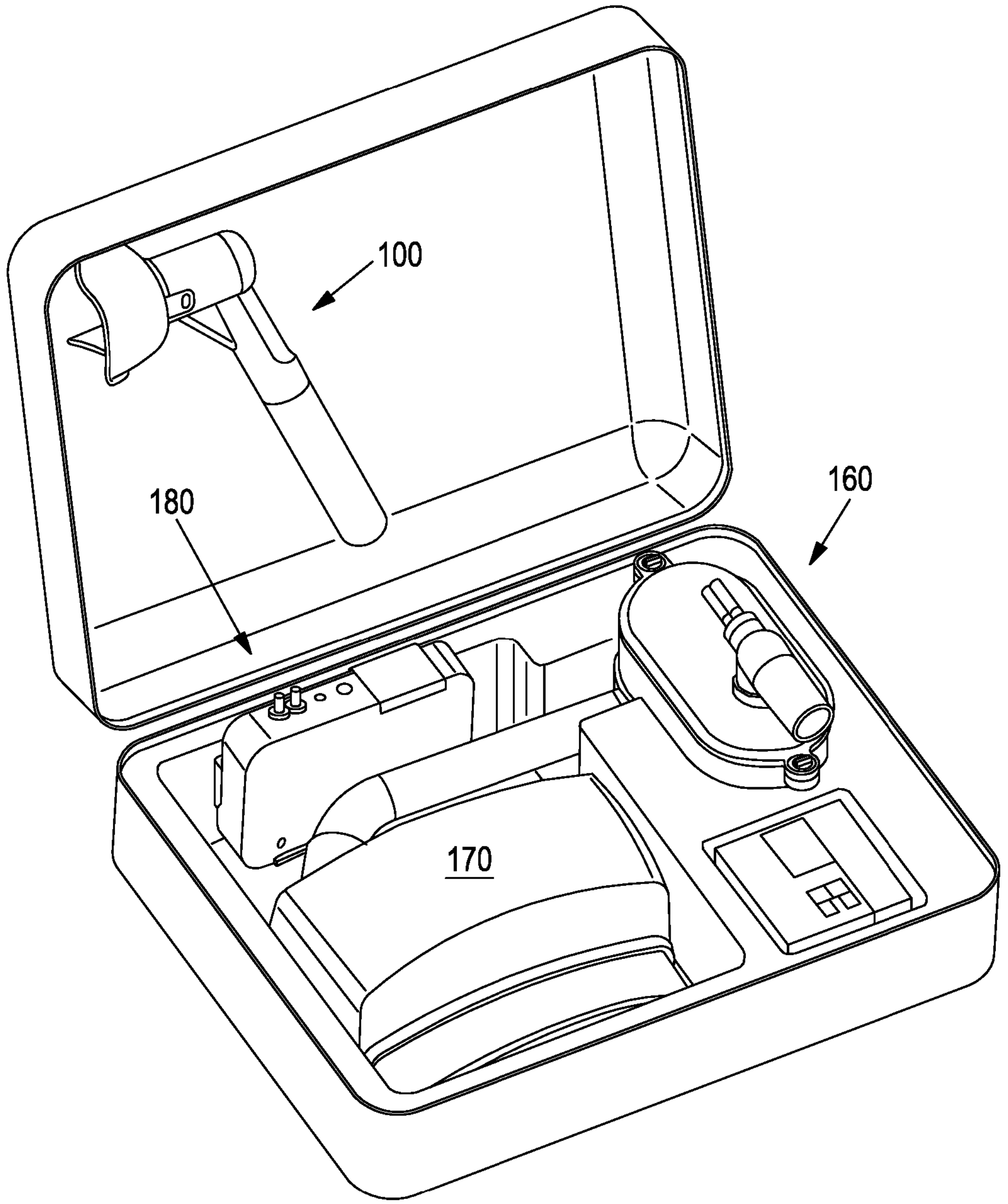
FIG. 12 shows a breath sampling system including a breath sampling device, an air pump, an air purification system and a controller.

FIG. 12 shows a breath sampling system comprising: a breath sampling device 100, air purifier 160, air pump 170 and controller 180. The breath sampling device 100 may, for example, be as shown in FIGS. 1 to 5, and the air purifier may be as shown in FIGS. 6 and/or 7. The air pump 170 is connectable to the air purifier 160 to pump air through the air purifier 160 for supply to the breath sampling device 100. A positive pressure may thereby be maintained in the breath sampling device 100 while it is in place on a patient's face. A controller 180 is provided, comprising a sampling pump, pressure sensor and control logic (such as a microprocessor). The controller 180 comprises a sampling port and a pressure port, respectively for connection to the sample conduit 134 and the pressure conduit 132. The controller may be configured to pump a sample of breath into the sample container during a particular, preselected, portion of the patient's breathing cycle. For example the end tidal portion of a breath cycle may be targeted for sampling, based on a variation in pressure detected by the pressure sensor via the pressure conduit 132.

Figure 13:
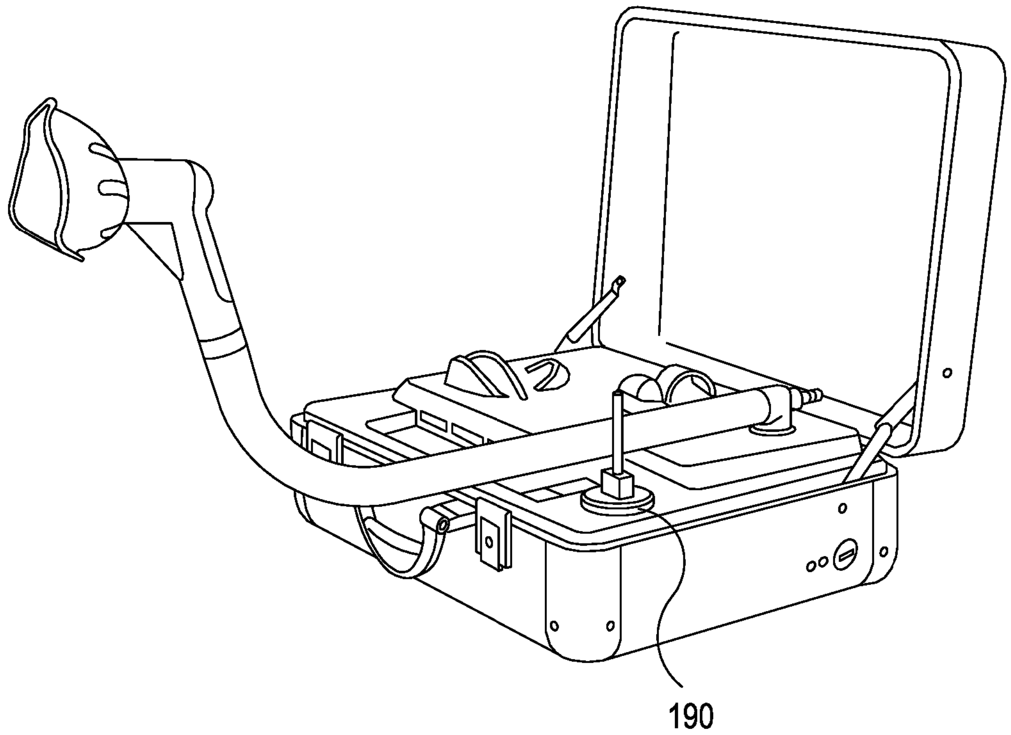
FIG. 13 shows an example breath sampling system (BreathTrace) similar to that of FIG. 12, further including a quality control system.

FIG. 13 shows an alternative breath sampling system (BreathTrace) similar to that of FIG. 12. As in FIG. 12, the breath sampling system comprises: a breath sampling device, an air purifier, air pump and controller. The breath sampling system of FIG. 13 further comprises a quality control system 190. A thermal desorption tube can be positioned in the port of the quality control system 190. The quality control system 190 includes a valve that is connected to the controller. This enables the collection of environmental samples or system blank samples with the system.

Figure 14:
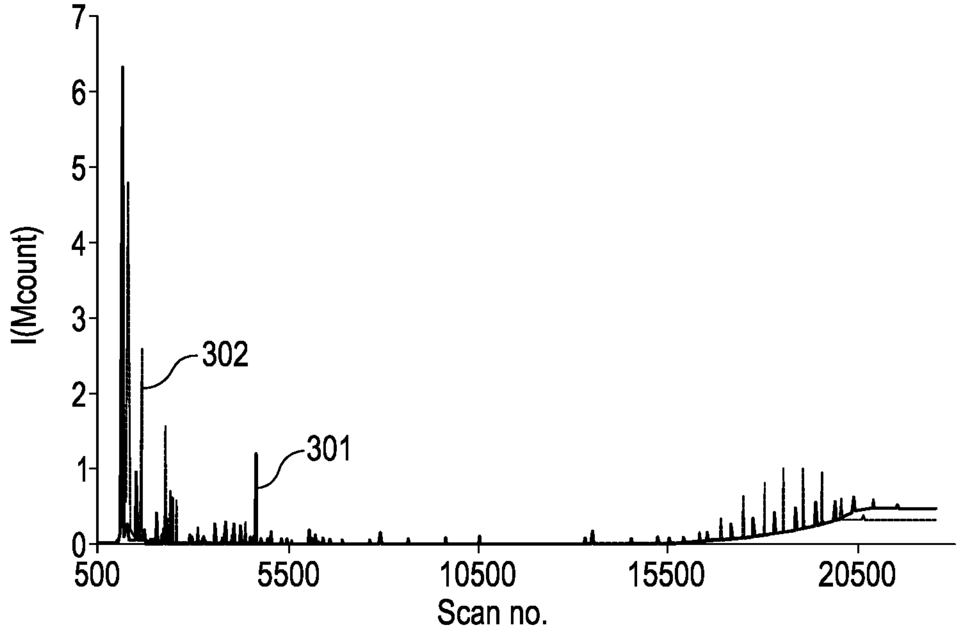
FIGS. 14 and 15 show a GC-MS analysis, comparing results obtained from a breath sampling system according to an embodiment with results obtained from a breath sample obtained using a prior art device.
Figure 15:
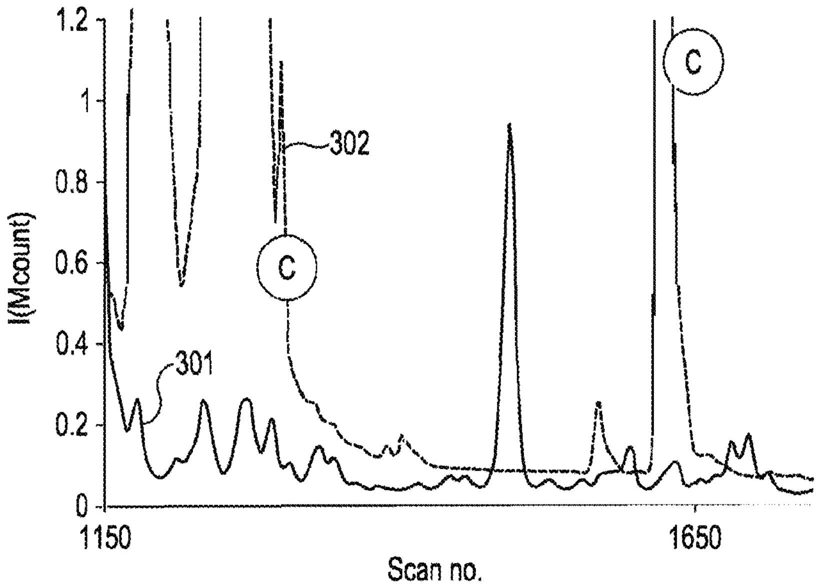

FIGS. 14 and 15 illustrate example results obtained by GC-MS analysis of samples obtained in accordance with an embodiment 301, compared with results obtained using a market leading existing breath sampling device 302. The results 302 from the prior art breath sampling device include contamination from collected water, which may interact with active phases in thermal desorption traps and stationary phases in a gas chromatography column to produce cyclic siloxanes. This may lead to the continuous and irreversible process of hydrolysis and degradation of analytical components, leading to variations in retention time and separation of features that may be useful as biomarkers. The variation complicates data modelling and reduces the likelihood of discovery of and effectiveness and accuracy of potential biomarkers. The sampler 110 provides more isokinetic sampling, which reduces the amount of water collected, and protects the sample container 113 from contact with the operator, reducing the potential for VOCs associated with gloves to be included in the analysed sample. This improvement can clearly be seen in comparing the results 301, 302. The results obtained from the market leading prior art device include contaminant features C that are associated with water retention in the collected breath samples, which is avoided in certain embodiments.

Figure 16:
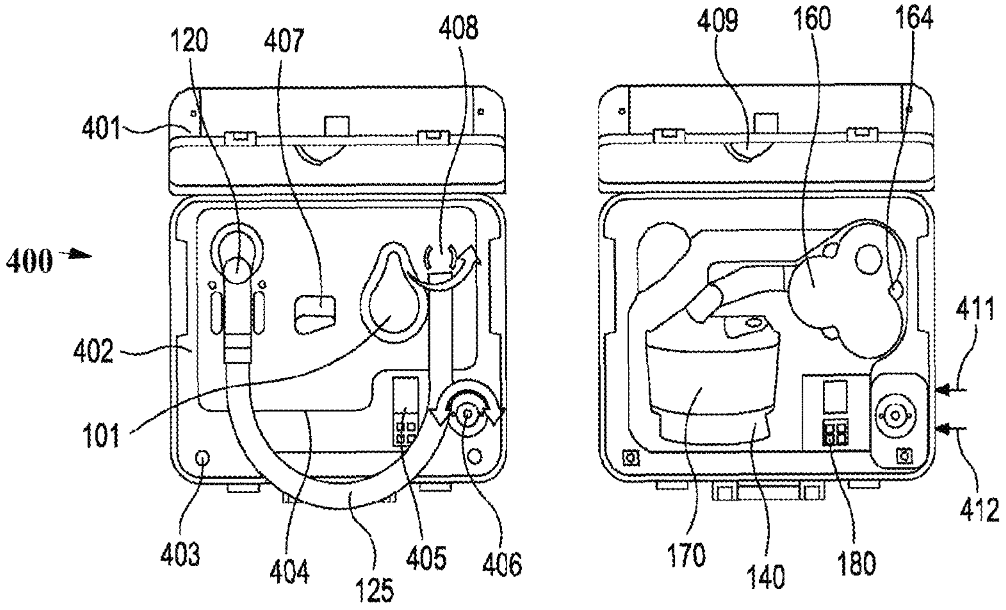
FIG. 16 shows an example breath sampling system similar to that of FIG. 13, in which the breath sampling system may be housed in one container or housing such as a briefcase.

FIG. 16 shows a breath sampling system 400 similar to that of FIG. 13. As shown in this example, the breath sampling system may be housed in one container or housing such as a briefcase 401. In other examples, the housing may take other forms, such as a box with a removable lid. The left-hand side figure shows the example system 400 as it would be presented during operation, with the lid of the briefcase 401 open. The right hand-side figure shows the system 400 with the face plate 402 removed, exposing the internals of the system 400 contained in the lower half of the briefcase 401.

When not removed, the face plate 402 is secured to the briefcase using screws 403. In other embodiments the internal face plate may be secured with other mechanisms, for example rotating cam locks or latches. The face plate 402 of FIG. 16 is configured to allow operation of the system 400 while in place. The face place 402 comprises an air supply intake 404. The internal face plate is configured to allow the user to operate the sample pump controls 405, a selector dial 406 and the air supply on/off button 407.

In the example of FIG. 16, the internal face plate 402 is further configured to allow a conduit joint 408 to pass through the face plate 402. The conduit joint 408 fluidly couples the air purifier 160 and intake conduit 125. The conduit joint 408 may be decoupled from the air purifier 160 when the face plate 402 is removed. In some embodiments, the conduit joint 408 may be attached with a twist locking mechanism or a thread screw.

The housing 401 or face plate 402 may be configured to hold the handle of the device to obtain a breath sample 120 or mask 101, when the housing 401 is closed or open. The face plate of figure comprises indents in which the handle 120 and mask 101 can be stored. In addition, the lid of the briefcase 401 comprises a holding fixture 409. This may be used to hold the handle 120 and mask 101 while they are connected during operation.

Under the face plate 402 the briefcase 401 also houses the air supply 170 and sample pump 180. Removing the face plate 402 also allows the user to access the air filter 160 locking mechanism 164, if for example a filter cartridge needs replacing, or the air supply battery release button 410.

The system 400 may also include a pump charging connector 411 and a USB laptop connector 412, which can be accessed through the housing 401.

According to an embodiment, the selector dial 406 is configured to operate a mode selection valve. In one example, the selector dial 406 has two positions, corresponding to two operating modes of the mode selection valve. In the first position, the selection valve fluidly couples the sample pump 180 with a port in order to sample ambient air. A sample container may be inserted into the port for obtaining an ambient air sample. In the second position the mode selection valve fluidly couples the sample pump with a sample conduit situated inside the intake conduit 125, so that a sample of the patient's breath may be obtained in a sample container. Such a selector dial 406 and mode selection valve allows the example system to take ambient or environmental samples and samples of the patient's breath.

Figure 17:
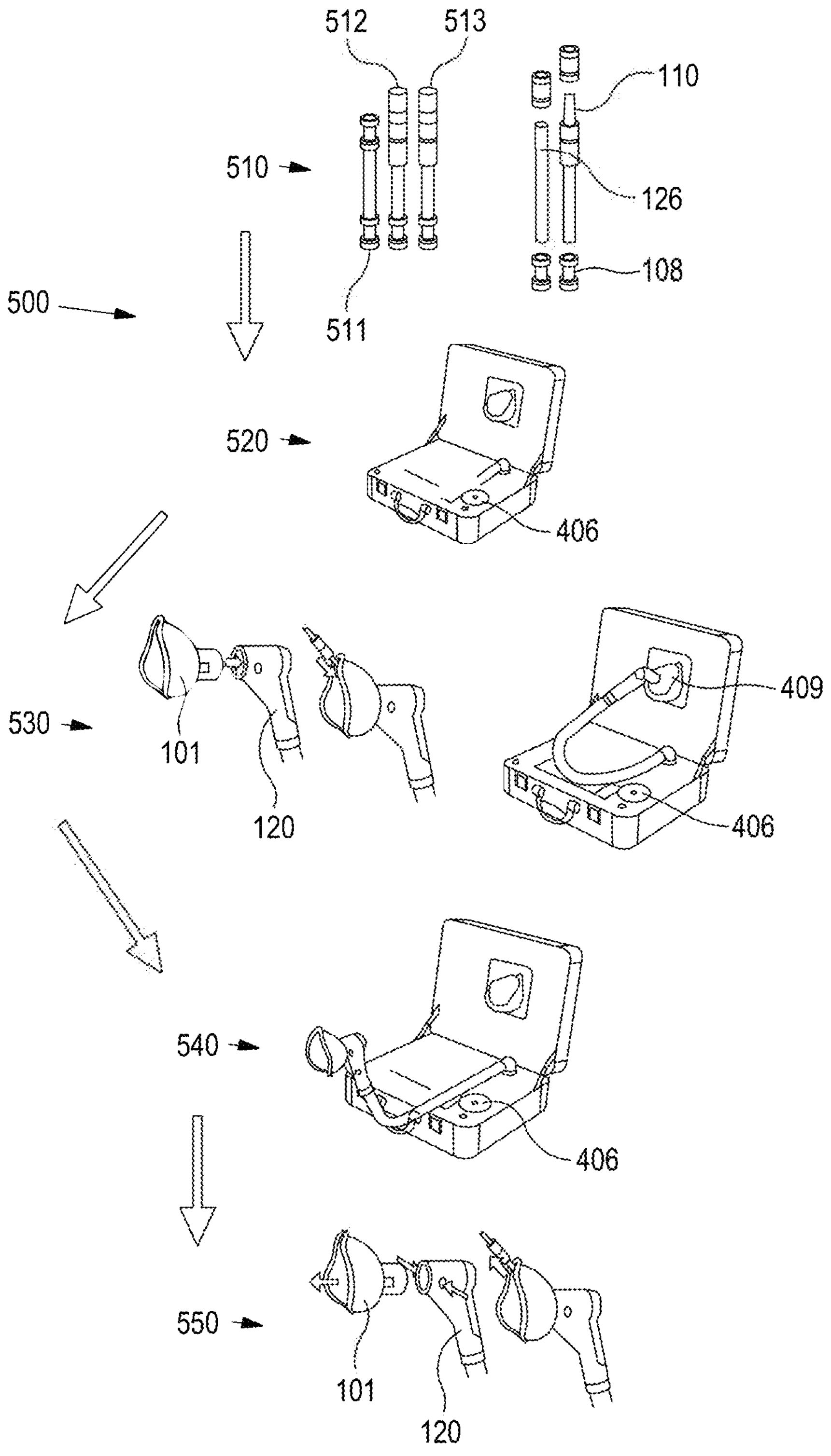
FIG. 17 shows an example breath sample collection method using a breath sampling system similar to that of FIG. 16.

FIG. 17 shows an example method 500 of using a breath sampling system (for example the system shown in FIG. 16) to obtain breath samples.

The breath sample collection method 500 of FIG. 17 comprises the following stages:

i) Pre-sampling 510, comprising testing the inventory to be used; disinfecting the system, allowing to dry and noting disinfectant used; checking tubes and ensuring sampling containers are securely capped;

ii) Environmental test 520, comprising setting the system selector dial 406 to the correct position (the first position); turning on the air supply; turning on the sampler pump; starting the software app; inserting thermal desorption tube 511; pressing app sample button to cause air to flow into the thermal desorption tube 511;

iii) Control test 530, comprising setting the system selector dial 406 to the correct position (the second position); inserting a new mask 101 and handset filter; inserting thermal desorption tube 512 with head 110; pressing app sample button (to cause air to flow into the control thermal desorption tube 512; removing and capping 108 thermal desorption tube 512;

iv) Breath test 540, comprising inserting new thermal desorption tube 513 with head 110; allowing patient to try mask 101 for comfort; pressing learn button on app; press app start button to cause breath to be sampled into the thermal desorption tube 513; removing and capping thermal desorption tube 513; removing mask 101 and filter; and v) Post-sampling 550, comprising removing the sample container from the breath sampling device; storing samples in fridge; recording results and outcomes as required.

At the beginning of the control test 530, the mask 101 may be attached to the handle of the device to obtain a breath sample 120. The mask 101 may be removed from handle at the end of the breath test 540. During the control test 530 the mask 101 and handle 120 may be stowed in the handle fixture 409.

In some examples, the samples may be taken: an environmental sample 511; a control sample 512; and a breath sample 513. Samples may be collected in contains such as thermal desorption tubes. The containers may comprise a cap 108 and a sampler head 110. The head 110 may be attached to the tube or container with a groove 126.

Although specific embodiments have been described, variations are possible, and the scope of protection should be determined with reference to the appended claims.

The invention claimed is:

1. A device for obtaining a breath sample from a patient, comprising:

a mask or mouthpiece for receiving breath from the patient;

an outlet through which breath is exhausted from the device;

a sampler, comprising:

a distal portion configured to protrude into a flow of breath from the mask or mouthpiece, a sampler opening in the distal portion for obtaining a breath sample;

a sample container in communication with the sampler for receiving the breath sample from the sampler; and a handle for holding the device, wherein the sample container is housed within the handle and the sampler is housed by the handle.

2. The device of claim 1, wherein the sampler opening is disposed in a sidewall of the distal portion.

3. The device of claim 2, wherein the sampler opening is spaced apart from a tip of the distal portion.

4. The device of claim 3, wherein a tip of the distal portion comprises an end flange.

5. The device of claim 1, wherein the sampler comprises a proximal portion configured to engage with the sample container.

6. The device of claim 5, wherein the proximal portion of the sampler is configured to seal against an outside of the sample container.

7. The device of claim 6, wherein the sampler comprises an internal groove and an O-ring seal disposed in the internal groove for forming a seal with the outside of the sample container.

8. The device of claim 1, wherein the sample container is removeable from the device by pulling on the sampler.

9. The device of claim 1, further comprising a filter between the mask and the outlet.

10. The device of claim 1, wherein the sampler is configured for sealing engagement with the handle.

11. The device of claim 1, wherein the handle comprises a hand operable clip for locking and unlocking engagement of the handle with the mask or mouthpiece.

12. The device of claim 11, wherein the handle comprises an inner sleeve and an outer sleeve, and the handle is securable to the mask or mouthpiece by clamping the mask or mouthpiece between the inner and outer sleeve.

13. The device of claim 1, wherein the handle comprises a pressure probe for communicating a fluid pressure to a pressure sensor.

14. The device of claim 1, wherein the handle comprises an intake air conduit, for providing to the mask or mouthpiece for the patient to breath.

15. A breath sampling system, comprising the device of claim 1, and an air purifier comprising at least one cartridge filter configured to purify air provided to the breath sampling device.

16. The breath sampling system of claim 15, wherein the air purifier comprises two cartridge filters, configured for parallel flow.

17. The breath sampling system of claim 16, further comprising a hand operated latch for obtaining access to the cartridge filters for replacement of the cartridge filters.

18. The breath sampling system of claim 15, further comprising:

a controller comprising a sample port and a sample pump configured to draw air through the sample port;

a mode selection valve in fluid communication with the sample pump;

a sample conduit connecting the mode selection valve to the sample container;

a port for connection to a further sample container, for sampling ambient air;

wherein the mode selection valve is operable to selectively connect the sample pump with the sample conduit to sample breath into the sample container or to connect the sample pump with the port to sample ambient air into the further sample container.

* * * * *